(12) United States Patent
Benden et al.

(10) Patent No.: US 12,605,118 B2
(45) Date of Patent: Apr. 21, 2026

(54) PASSIVE SENSOR SYSTEMS FOR PERIPHERAL INPUT DEVICES AND THE USE THEREOF

(71) Applicant: The Texas A&M University System, College Station, TX (US)

(72) Inventors: Mark E. Benden, College Station, TX (US); Joohyun Rhee, College Station, TX (US)

(73) Assignee: The Texas A&M University System, College Station, TX (US)

( * ) Notice: Subject to any disclaimer, the term of this patent is extended or adjusted under 35 U.S.C. 154(b) by 829 days.

(21) Appl. No.: 17/641,397

(22) PCT Filed: Sep. 9, 2020

(86) PCT No.: PCT/US2020/049865

§ 371 (c)(1),
(2) Date: Mar. 8, 2022

(87) PCT Pub. No.: WO2021/050495

PCT Pub. Date: Mar. 18, 2021

(65) Prior Publication Data

US 2022/0296168 A1 Sep. 22, 2022

Related U.S. Application Data

(60) Provisional application No. 62/898,442, filed on Sep. 10, 2019.

(51) Int. Cl.
*A61B 5/00* (2006.01)
*A61B 5/01* (2006.01)
(Continued)

(52) U.S. Cl.
CPC .......... *A61B 5/6897* (2013.01); *A61B 5/0004* (2013.01); *A61B 5/0022* (2013.01);
(Continued)

(58) Field of Classification Search
CPC ..... A61B 5/6897; A61B 5/332; A61B 5/0004; A61B 5/0022; A61B 5/0024; A61B 5/01; A61B 5/02416; A61B 5/0533
See application file for complete search history.

(56) References Cited

U.S. PATENT DOCUMENTS

2011/0015504 A1* 1/2011 Yoo ..................... A61B 5/6897
600/301
2013/0317318 A1* 11/2013 Tartz ................... A61B 5/7221
600/301
(Continued)

*Primary Examiner* — Linda C Dvorak
*Assistant Examiner* — Abigail Bock
(74) *Attorney, Agent, or Firm* — Jackson Walker LLP

(57) ABSTRACT

The biometric and performance monitoring system includes a computer having a mouse and a keyboard electronically coupled thereto. A first sensor is disposed in the mouse, and is electrically coupled to the computer. A second sensor is disposed in the keyboard and is electrically coupled to the computer. The first sensor and the second sensor measure biometric parameters of a user. A computer-readable storage medium is associated with the computer and is adapted for storing the biometric parameters and the performance parameters. The computer measures performance parameters associated with the mouse and with the keyboard. The computer at least one of provides an alert to the user, electronically communicates with a medical service provider, and electronically communicates with a supervising entity responsive to analysis of changes in the biometric parameters and the performance parameters.

17 Claims, 6 Drawing Sheets

(51) Int. Cl.
| | |
|---|---|
| *A61B 5/024* | (2006.01) |
| *A61B 5/0533* | (2021.01) |
| *A61B 5/332* | (2021.01) |

(52) U.S. Cl.
CPC .............. *A61B 5/0024* (2013.01); *A61B 5/01* (2013.01); *A61B 5/02416* (2013.01); *A61B 5/0533* (2013.01); *A61B 5/332* (2021.01)

(56)                    References Cited

U.S. PATENT DOCUMENTS

| 2013/0338539 A1* | 12/2013 | Bailey ................. A61B 5/1101 600/595 |
|---|---|---|
| 2014/0163336 A1 | 6/2014 | Horseman |
| 2019/0090816 A1* | 3/2019 | Horseman ............ A61B 5/7282 |

\* cited by examiner

*104*

206

203

204

201

202

PASSIVE SENSOR SYSTEMS FOR PERIPHERAL INPUT DEVICES AND THE USE THEREOF

CROSS-REFERENCE TO RELATED APPLICATIONS

This application claims priority to, and incorporates by reference, U.S. Provisional Patent Application No. 62/898,442, filed on Sep. 10, 2019.

TECHNICAL FIELD

The present disclosure relates generally to biometric scanning and more particularly, but not by way of limitation, to passive biometric scanning utilizing embedded sensors in computer peripheral input devices and determination of health-related condition changes of a user.

BACKGROUND

This section provides background information to facilitate a better understanding of the various aspects of the disclosure. It should be understood that the statements in this section of this document are to be read in this light, and not as admissions of prior art.

Employee impairment is a serious concern for employers. In various industries, impairment of employees can impact, not only a business's productivity, but the health, safety, and well-being of other employees as well as the general public. For this reason, employers have an interest of being notified of possible employee impairment for reasons such as exhaustion, physical or mental illness, addiction, or other type of impairment. Such notification affords employers an opportunity to address potentially dangerous situations and, if needed, provide intervention and support to the impaired employee.

SUMMARY

Aspects of the disclosure relate to a biometric and performance monitoring system. The biometric and performance monitoring system includes a computer having a mouse and a keyboard electronically coupled thereto. A first sensor is disposed in the mouse, and is electrically coupled to the computer. A second sensor is disposed in the keyboard and is electrically coupled to the computer. The first sensor and the second sensor measure biometric parameters of a user. Performance parameters related to use of the mouse of the user are also measured and transmitted to the computer. A computer-readable storage medium is associated with the computer and is adapted for storing the biometric parameters and the performance parameters. The computer at least one of provides an alert to the user, electronically communicates with a medical service provider, and electronically communicates with a supervising entity responsive to analysis of changes in the biometric parameters and the performance parameters.

Aspects of the disclosure relate to a method of evaluating performance of a user. The method includes obtaining, via at least one of a first sensor and a second sensor, biometric parameters from a user. The biometric parameters are stored in a computer-readable storage medium associated with a computer that is electronically coupled to the first sensor and the second sensor. Performance parameters associated with a mouse are obtained and transmitted to the computer. A base-line data set is determined from the biometric parameters and the performance parameters. The biometric parameters and the performance parameters are analyzed to determine variations from the base-line data set. Responsive to a determined variation from the base-line data set, at least one of a user, a medical service provider, and a supervising entity is alerted to possible user impairment.

Aspects of the disclosure relate to a biometric and performance monitoring system. The biometric and performance monitoring system includes a computer having a mouse and a keyboard electronically coupled to the computer. A first sensor is disposed in the mouse. The first sensor is electrically coupled to the computer. A second sensor is disposed in the keyboard. The second sensor is electrically coupled to the computer. The first sensor and the second sensor measure biometric parameters of a user. A computer-readable storage medium is associated with the computer. The computer-readable storage medium is adapted for storing the biometric parameters and the performance parameters. The computer measures performance parameters associated with the mouse and with the keyboard. The computer determines a base-line data set from the biometric parameters and the performance parameters and alerts at least one of a user, a medical service provider, and a supervising entity of possible user impairment responsive to a determined variation from the base-line data set.

This summary is provided to introduce a selection of concepts that are further described below in the detailed description. This summary is not intended to identify key or essential features of the claimed subject matter, nor is it intended to be used as an aid in limiting the scope of claimed subject matter.

BRIEF DESCRIPTION OF THE DRAWINGS

The disclosure is best understood from the following detailed description when read with the accompanying figures. It is emphasized that, in accordance with standard practice in the industry, various features are not drawn to scale. In fact, the dimensions of various features may be arbitrarily increased or reduced for clarity of discussion.

DETAILED DESCRIPTION

Various embodiments will now be described more fully with reference to the accompanying drawings. The disclosure may, however, be embodied in many different forms and should not be construed as limited to the embodiments set forth herein.

Figure 1:
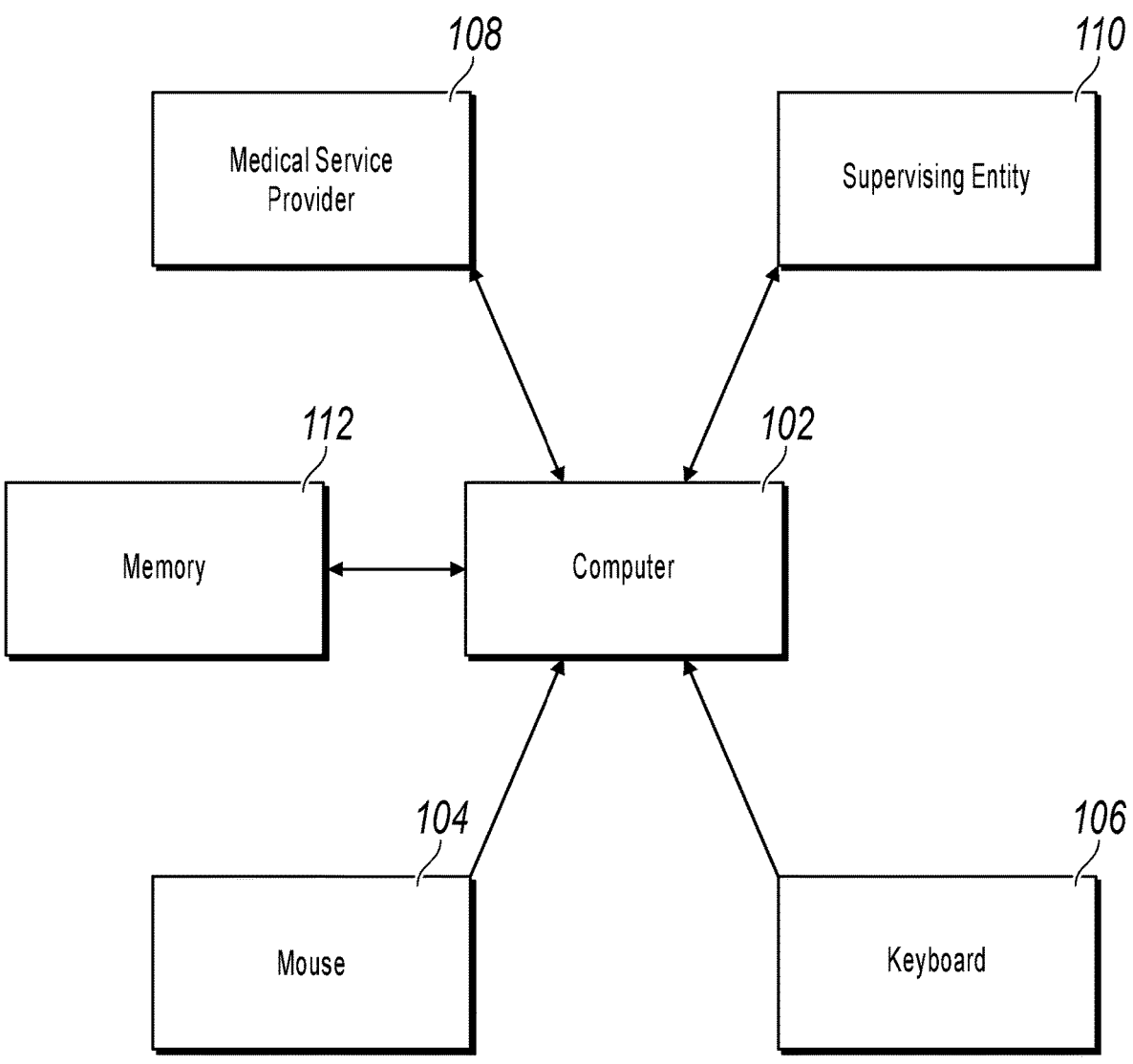
FIG. 1 is block diagram of a biometric monitoring system according to aspects of the disclosure.

FIG. 1 is block diagram of a biometric and performance monitoring system 100. The biometric and performance monitoring system 100 includes a computer 102 having a plurality of peripheral input devices. In various embodiments, the peripheral input devices may be, for example, a mouse 104 and a keyboard 106; however, in other embodiments the peripheral input devices could be any type of computer input device such as, for example, a track ball, a vertical mouse, a touch screen, or any other type of computer input device. In the embodiment shown, the mouse 104 and the keyboard 106 include biometric sensors that are capable of measuring various biometric parameters and transmitting the measured biometric parameters to the computer 102. The mouse 104 also transmits performance parameters related to the user's utilization of the mouse 104 to the computer 102. In various embodiments, the transmission of the biometric parameters between the mouse 104 and the keyboard 106 to the computer 102 is via a wired connection; however, in other embodiments, the biometric sensors may communicate with the computer 102 via a wireless protocol. The computer 102 interprets the biometric parameters and analyzes the biometric parameters within the context of the performance parameters for indications of impairment of a user utilizing the computer 102. The computer 102 is electronically coupled to at least one of a medical service provider 108 and a supervising entity 110. In various embodiments, the medical service provider 108 and the supervising entity 110 are located remotely from the biometric and performance monitoring system 100; however, in other embodiments, the medical service provider 108 and the supervising entity 110 may be located at the same facility as the biometric and performance monitoring system 100. In various embodiments, the biometric and performance monitoring system 100 communicates with the medical service provider 108 and the supervising entity 110 via a wired connection; however in other embodiments, the biometric and performance monitoring system 100 may communicate with the medical service provider 108 and the supervising entity 110 via a wireless protocol. In other embodiments, the biometric and performance monitoring system 100 may provide an alert to the user thereby allowing the user an opportunity to self-correct or seek third-party assistance.

Figure 2:
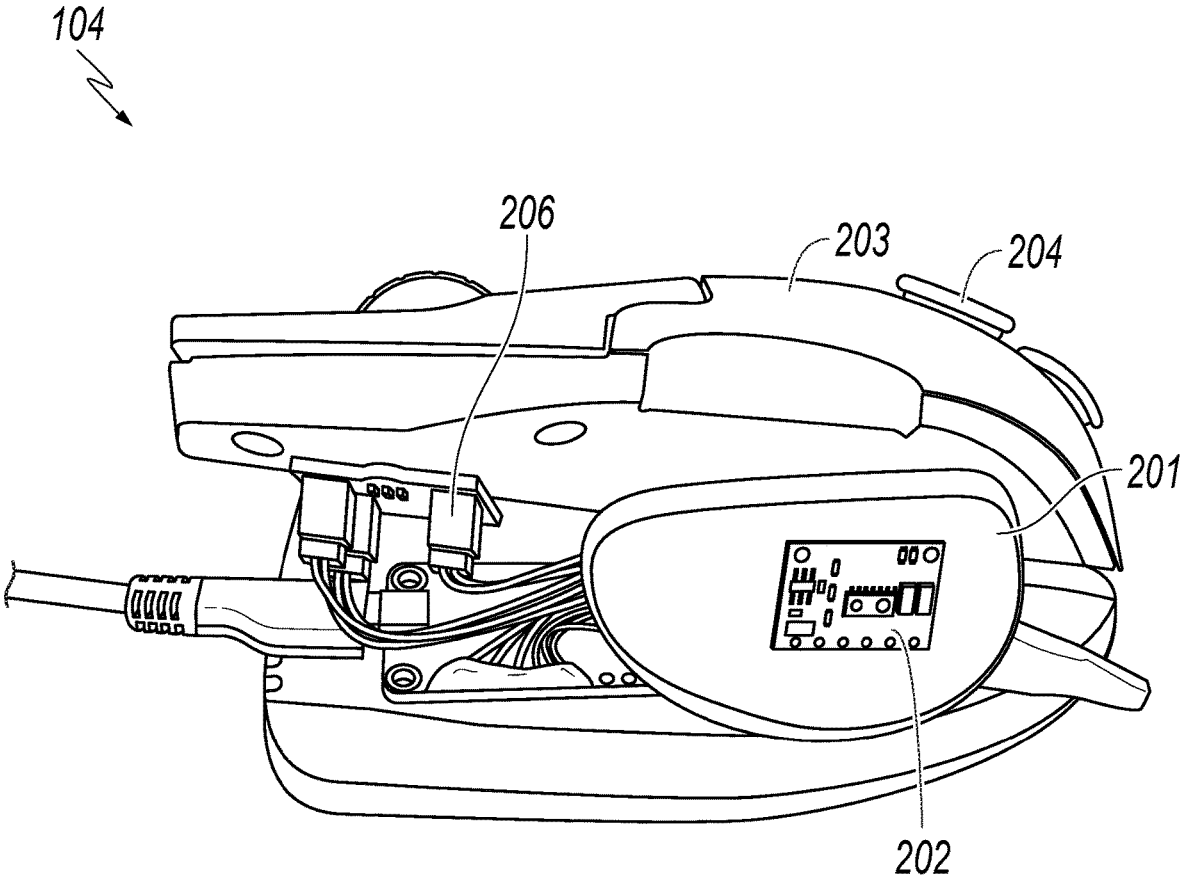
FIG. 2 is a side view of an exemplary mouse including biometric sensors according to aspects of the disclosure.
Figure 3:
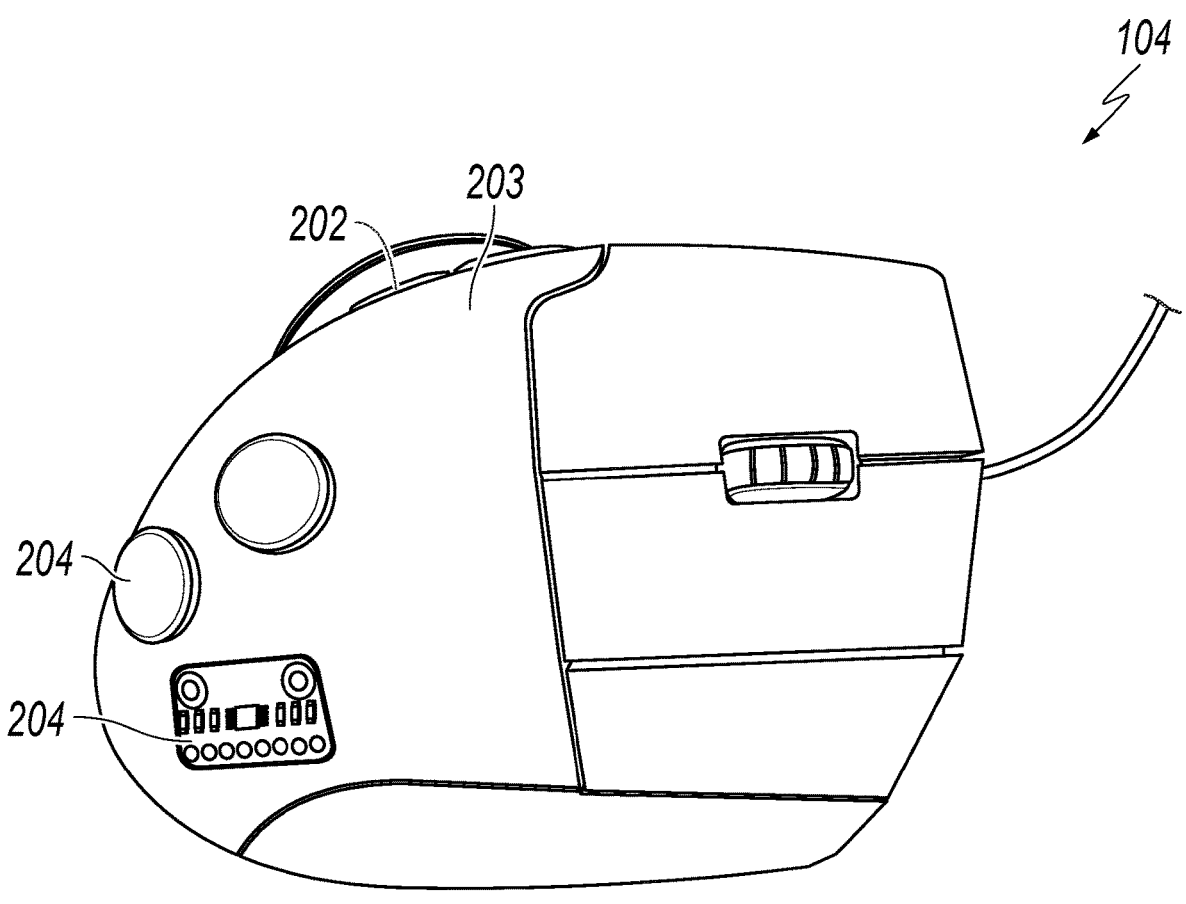
FIG. 3 is a top view of an exemplary mouse including biometric sensors according to aspects of the disclosure.

FIG. 2 is a side view of the mouse 104 including biometric sensors. FIG. 3 is a top view of the mouse 104 including the biometric sensors. Referring to FIGS. 2-3 collectively, the mouse 104 includes a first sensor 202 disposed on a side surface 201 of the mouse 104 and a second sensor 204 disposed on a top surface 203 of the mouse 104. In various embodiments, the first sensor 202 may be, for example, a skin-temperature sensor or a pulse oximeter. The second sensor 204 may be, for example, a galvanic-skin resistance ("GSR") sensor that measures electro-dermal resistance between two points. The embodiment illustrated in FIGS. 2-3 illustrates the first sensor 202 and the second sensor 204; however, in other embodiments, the mouse 104 may include any number of sensors. Additionally, the embodiment illustrated in FIGS. 2-3 shows the first sensor 202 and the second sensor 204 being disposed on the side surface 201 and the top surface 203 of the mouse 104, respectively. In other embodiments, the first sensor 202 and the second sensor 204 may be disposed at any location on the mouse 104 so as to facilitate sufficient contact with the skin of the user.

Additionally, the mouse 104 includes an accelerometer 206 such as, for example, a three-axis accelerometer, to measure performance parameters including, for example, acceleration patterns of the mouse 104. The computer 102 also tracks key-logging information, movement information, click-rate information, and error rates related to use of the mouse 104. In various embodiments, the accelerometer 206 is disposed within the mouse 104. The performance parameters are transmitted from the mouse 104 of the computer 102. In various embodiments, the performance parameters relating to use of the mouse 104 may include, for example, mouse strain exposure, hours of computer usage, number of breaks skipped, a degree that breaks where postponed, mouse clicks, distance the mouse has moved (in pixels), number of mouse double clicks, number of mouse left clicks, number of mouse right clicks, number of scroll clicks, minutes from midnight the first activity occurred, and minutes from midnight the last activity occurred.

Figure 4:
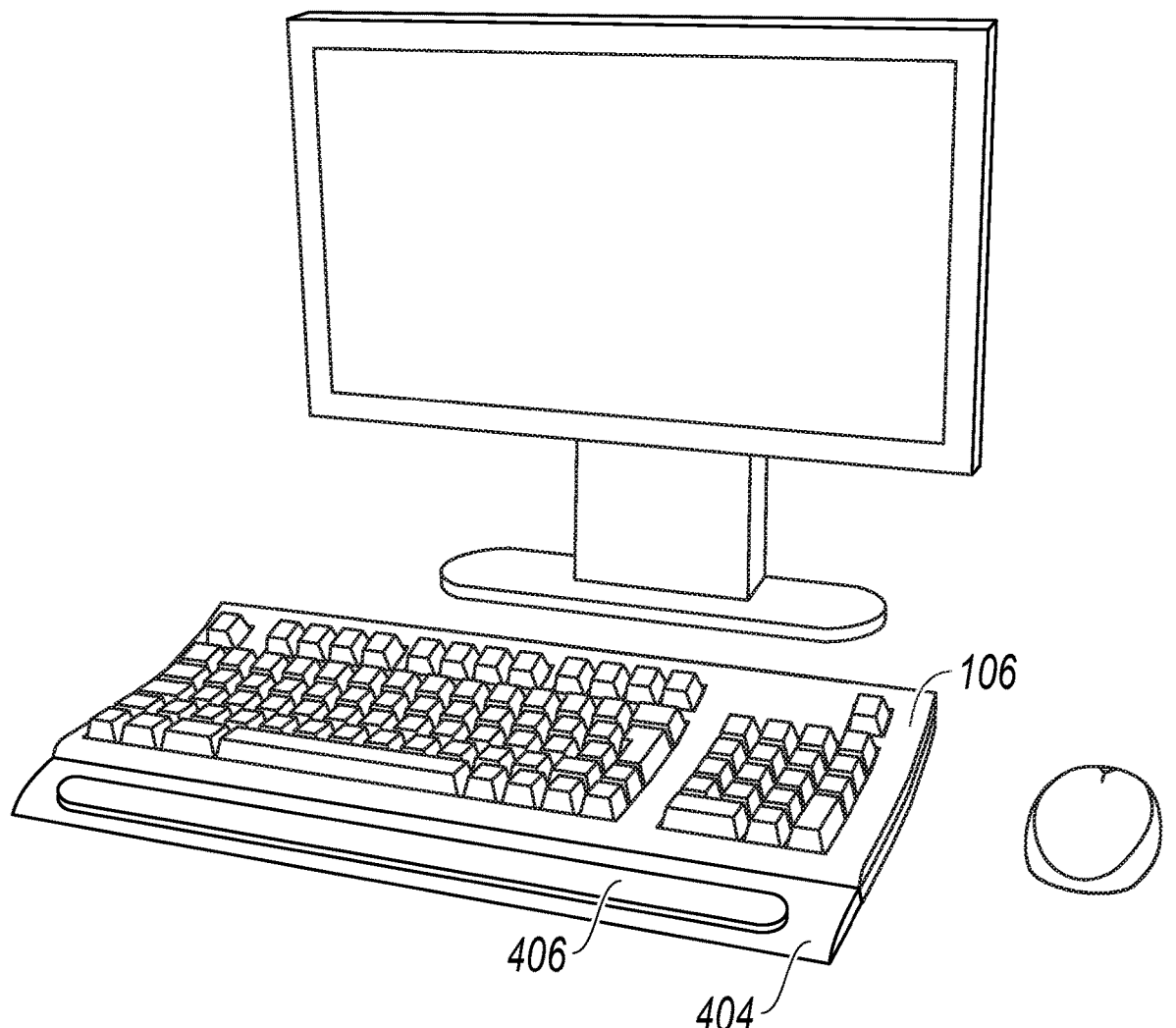
FIG. 4 is a top view of an exemplary keyboard including biometric sensors according to aspects of the disclosure.

FIG. 4 is a top view of the keyboard 106 including a third sensor 406. The keyboard 106 includes a wrist support 404, which has the third sensor 406 embedded therein. In various embodiments, the third sensor 406 is an electrocardiogram ("EKG"). In various embodiments, the third sensor 406 includes a conductive surface that is in contact with a skin of the user. In various embodiments, the third sensor 406 utilizes conductivity measurements of the user's skin to measure the user's heartrate and EKG data. The embodiment illustrated in FIG. 4 illustrates the third sensor 406 being located in the wrist support 404; however, in other embodiments, the third sensor 406 could be located elsewhere on the keyboard 106. Additionally, in various embodiments, the wrist support 404 may not be integral with the keyboard 106 but may be constructed separately from the keyboard 106. In various embodiments, the keyboard 106 may include other sensors to measure and record other biometric parameters of the user.

Still referring to FIG. 4, in various embodiments, the keyboard 106 may include sensors to track performance parameters of the user including, for example, a number of keystrokes per minute of the user. The computer 102 also tracks key-logging information and error rates related to use of the keyboard 106. The performance parameters measured by the keyboard 106 may include, for example, keyboard strain exposure, keyboard usage hours, words typed, average time keys are held down, hours of computer usage, number of breaks skipped, a degree that breaks were postponed, keypresses, number of backspace or delete key presses, a number of times a user switches between a keyboard and a mouse, minutes from midnight the first activity occurred, minutes from midnight the last activity occurred, words typed during PM hours, number of typographical errors during AM hours, and number of typographical errors during PM hours. In various embodiments, the keyboard 106 transmits the performance parameters to the computer-readable storage medium 112 of the computer 102.

Referring now to FIGS. 1-4, during operation, the first sensor 202 and the second sensor 204 disposed on the mouse 104 collect biometric parameters from the user including, for example, the user's skin temperature, a galvanic-skin resistance of the user, the user's heart rate, and the user's oxygen saturation. Additionally, the third sensor 406, disposed with the keyboard 106 obtains EKG data from the user. At the same time, the accelerometer 206 and the keyboard 106 collect performance parameters related to the user. The biometric parameters and the performance parameters measured by the first sensor 202, the second sensor 204, the third sensor 406, and the accelerometer 206 are transmitted to and stored on the computer 102. The computer 102 has a computer-readable storage medium 112 associated therewith, which stores the biometric parameters and the performance parameters from the first sensor 202, the second sensor 204, the third sensor 406, and the accelerometer 206. In various embodiments, the computer-readable storage medium 112 may be local or remote from the computer 102. The computer 102 includes an algorithm stored on a computer-readable medium. By employing the algorithm, the computer 102 analyzes the measurements from the first sensor 202, the second sensor 204, the third sensor 406 within the context of the performance parameters measured by and the accelerometer 206 and the keyboard 106 and determines a base-line data set for a particular user working under nominal, unimpaired conditions. The computer 102, utilizing the algorithm, is then able to analyze the biometric parameters and the performance parameters from the first sensor 202, the second sensor 204, the third sensor 406, and the accelerometer 206 to detect variations from the base-line data set that could be indicative of impairment of the user. When the computer 102 detects variations from the base-line data set that could be indicative of impairment, the computer 102 may initiate corrective action. The corrective action, in various embodiments, may include for example, notifying the supervising entity 110, notifying the medical service provider 108, or providing an alert to the user. In various embodiments, the computer 102 is able to analyze biometric parameters and performance parameters received from the first sensor 202, the second sensor 204, the third sensor 406, and the accelerometer 206 in real time or near real-time. As used herein, the term "near real time" means an instance of time that may include a delay typically resulting from processing, calculation and/or transmission times inherent in processing systems or web-based transmissions.

Figure 5:
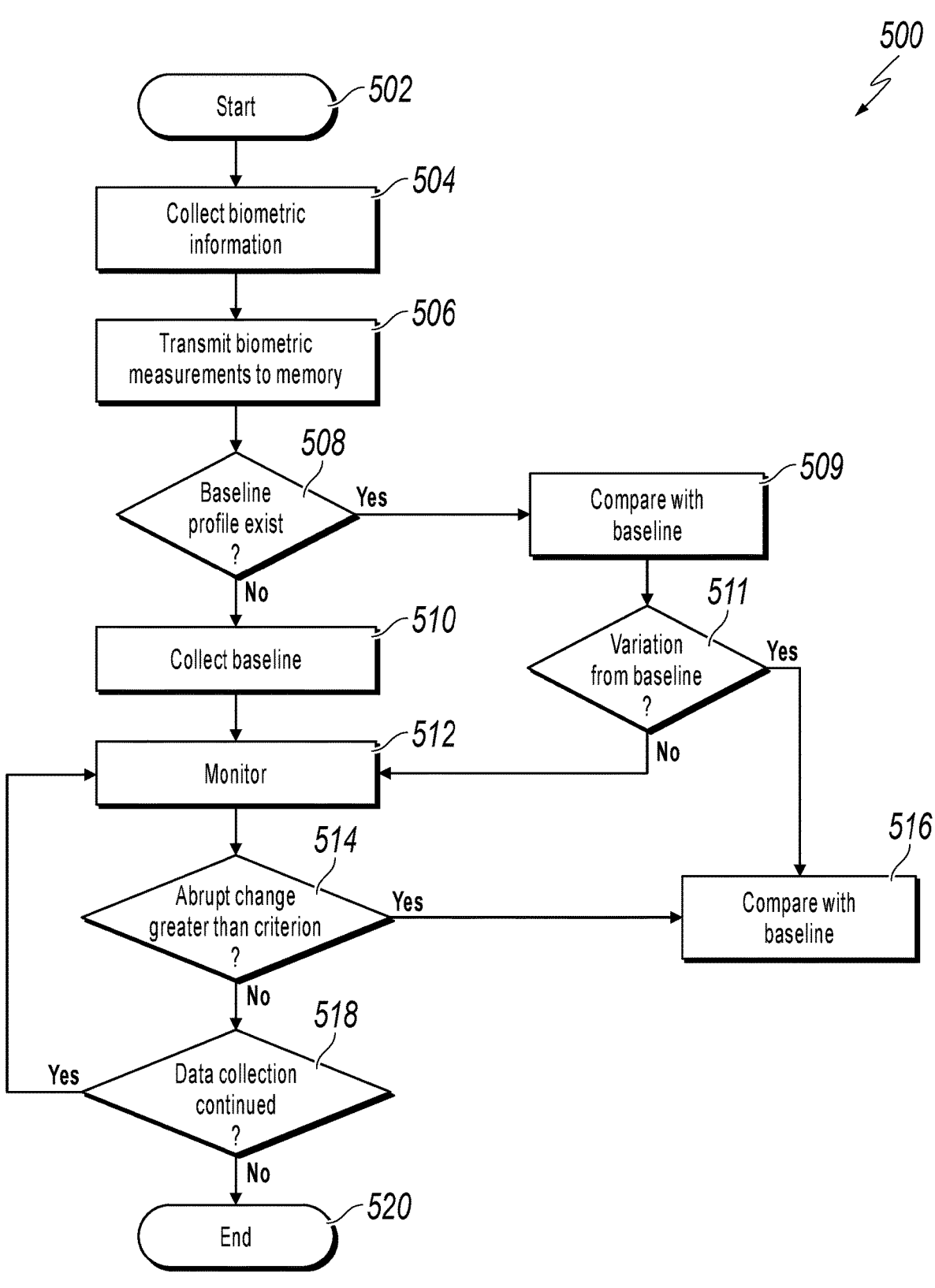
FIG. 5 is a flow diagram illustrating a process for biometric monitoring according to aspects of the disclosure.

FIG. 5 is a flow diagram illustrating a process 500 for biometric monitoring. The process 500 begins at step 502. At step 504, the first sensor 202, the second sensor 204, and the third sensor 406 collect biometric parameters from the user while the accelerometer 206 and the keyboard 106 collect performance parameters from the user. At step 506, the biometric parameters and the performance parameters obtained by the first sensor 202, the second sensor 204, the third sensor 406, and the accelerometer 206 are transmitted to the computer-readable storage medium 112 associated with the computer 102. At step 508, it is determined if a baseline performance profile exists for the user. If, at step 508, it is determined that a baseline performance profile does not exist for the user, then the process 500 proceeds to step 510 where the computer 102 analyzes the biometric parameters and the performance parameters obtained from the first sensor 202, the second sensor 204, the third sensor 406, and the accelerometer 206 and determines a base-line data set for a particular user working under nominal, unimpaired conditions. From step 510, the process 500 proceeds to step 512 where the computer 102 compares the biometric parameters and the performance parameters obtained from the first sensor 202, the second sensor 204, the third sensor 406, and the accelerometer 206 to the baseline performance profile. At step 514, it is determined if the biometric parameters and the performance parameters obtained from the first sensor 202, the second sensor 204, the third sensor 406, and the accelerometer 206 exhibit an abrupt change greater than a criterion. In various embodiments, the criterion may be unique to an individual user and may be determined through a data-analysis process including, for example, machine learning or artificial intelligence. In various embodiments, the criterion is analyzed in context of the user's position and type of work being performed. For example, a user having a heart rate of 120 bpm while seated at a desk may be indicative of a potentially serious medical condition. On the other hand, the same user having a heart rate of 120 bpm while performing strenuous activity may not be cause for alarm.

Still referring to FIG. 5, if, at step 514, it is determined that an abrupt change has occurred, the process 500 proceeds to step 516 where corrective action is initiated. At step 516, the corrective action may, in various embodiments, include notifying a supervising entity 110, notifying a medical service provider 108, or providing an alert to the user. If, at step 514, it is determined that an abrupt change has not occurred, the process 500 proceeds to step 518 where it is determined if collection of the biometric parameters and the performance parameters is to continue. In various embodiments, the determination to continue collection of the bio-metric parameters and the performance parameters may be based, for example, on activity of the user. For instance, if the computer 102 records no biometric parameters or performance parameters for a pre-determined time period, it may be assumed that the user has stepped away from the computer 102 or is performing other tasks not requiring use of the computer 102. In such instances, the computer 102 may discontinue collection of the biometric parameters and the performance parameters temporarily until usage is again detected. If, at step 518, it is determined that collection of the biometric parameters and the performance parameters is to continue, the process 500 returns to step 512. If, at step 518, it is determined that collection of the biometric parameters and the performance parameters is not to continue, the process 500 proceeds to step 520 where the process 500 ends.

If, at step 508, it is determined that a baseline performance profile does exist for the user, then the process 500 proceeds to step 509. At step 509, the computer 102 compares the biometric parameters and the performance parameters obtained from the first sensor 202, the second sensor 204, the third sensor 406, and the accelerometer 206 to the baseline performance profile. At step 511, the computer 102 determines if a variation from the base line performance profile has occurred. If, at step 511, it is determined that a variation from the base line performance profile has occurred, the process 500 proceeds to step 516 where corrective action is initiated. If, at step 511, it is determined that a variation from the base line performance profile has not occurred, the process 500 proceeds to step 512.

Figure 6:
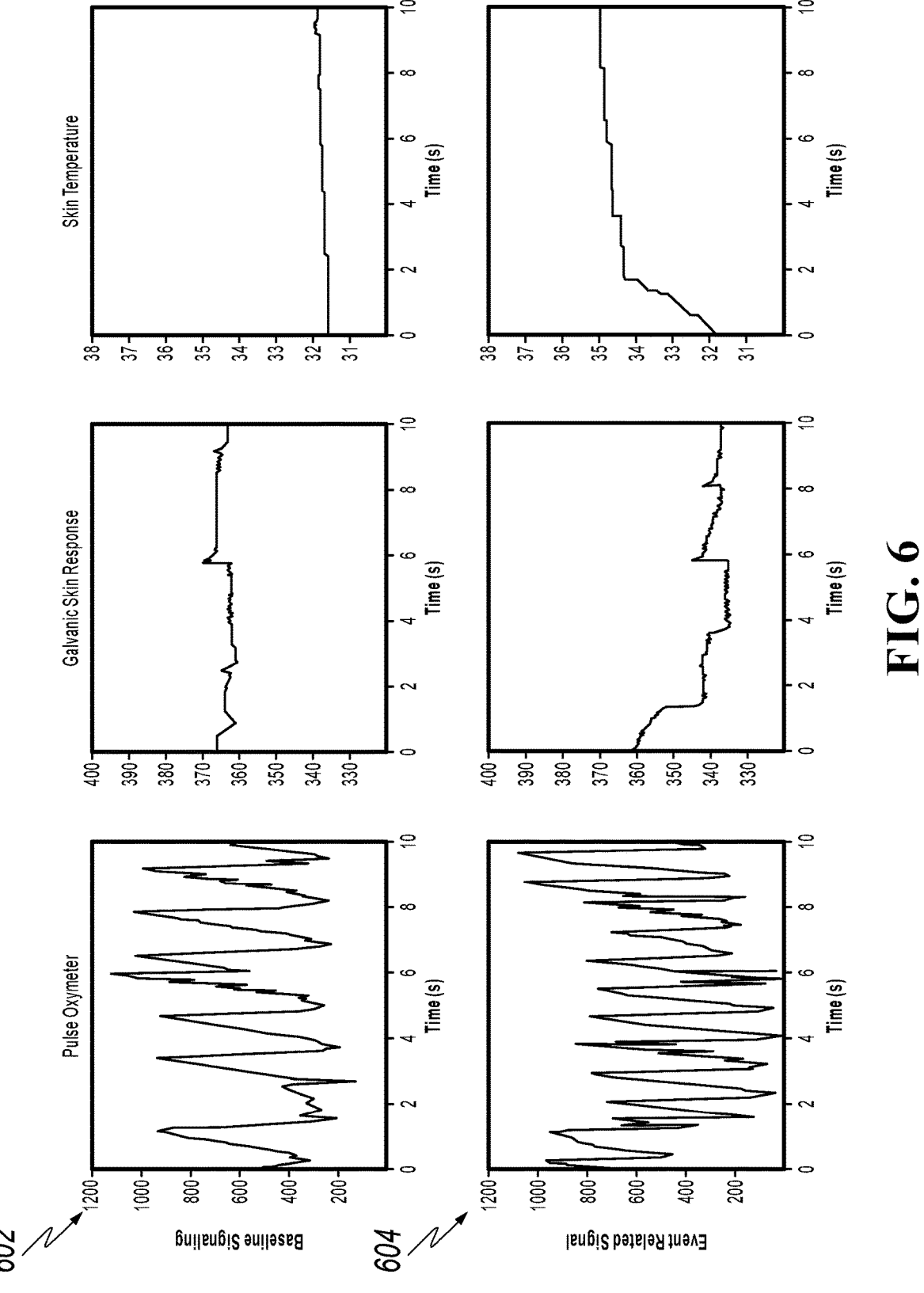
FIG. 6 is a graph of exemplary biometric data illustrating an impairing event according to aspects of the disclosure.

FIG. 6 is a graph of exemplary biometric parameters and performance parameters illustrating an established baseline performance profile (illustrated in region 602) and changes of the baseline performance profile related to any event. The region 602 illustrates the biometric parameters and the performance parameters before the event-related condition changes and the region 604 illustrates the biometric parameters and the performance parameters after the event-related condition change. When compared to region 602, the region 604 illustrates a marked increase or decrease in biometric measurements in the period during or after the impairing event. By way of example, region 604 illustrates signals that are typically indicative of a sympathetic nervous system being excited. The biometric parameters and the performance parameters illustrated in region 604 are indicative of elevated stress or sickness. This is based, at least in part, on increased heart rate (indicated by the pulse oximeter), decreased skin conductance, and increased skin temperature. During operation, a computer algorithm determines if changes in a signal pattern from at least one of the first sensor 202, the second sensor 204, the third sensor 406, and the accelerometer 206 indicates at least one of inhibition or excitation of the autonomic nervous system. In various embodiments, such a change in signal pattern may exhibit a clear or mixed indication. Further analysis is then performed combining biometric parameters and behavior-related performance parameters in an effort to determine a possible cause of the change in signal pattern. In various embodiments, the further analysis may be unique to an individual user. In such embodiments, the algorithm may establish a hierarchy and order of signal parameters that are evaluated. For instance, if the computer 102 detects an increase in body temperature, the computer 102 may next analyze if an increase in heart rate has occurred that could be indicative, for example, of a fever. In other embodiments, the computer 102 may utilize geographical information including, for example, known geographic locations where incidence of a particular illness is high. Similarly, a user exhibiting biometric parameters such as, for example, an elevated temperature alone may not be cause for concern. However, when the biometric parameter is analyzed within the context of performance parameters such as, decreased accuracy or slowed work pace, the totality of the biometric parameters and the performance parameters could be indicative of a condition such as illness-related fever or possible opioid use.

For purposes of this patent application, the term computer-readable storage medium encompasses one or more tangible computer-readable storage media possessing structures. As an example and not by way of limitation, a computer-readable storage medium may include a semiconductor-based or other integrated circuit (IC) (such as, for example, a field-programmable gate array (FPGA) or an application-specific IC (ASIC)), a hard disk, an HDD, a hybrid hard drive (HHD), an optical disc, an optical disc drive (ODD), a magneto-optical disc, a magneto-optical drive, a floppy disk, a floppy disk drive (FDD), magnetic tape, a holographic storage medium, a solid-state drive (SSD), a RAM-drive, a SECURE DIGITAL card, a SECURE DIGITAL drive, a flash memory card, a flash memory drive, or any other suitable tangible computer-readable storage medium or a combination of two or more of these, where appropriate.

The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," "generally," and "about" may be substituted with "within a percentage of" what is specified.

Depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. Although certain computer-implemented tasks are described as being performed by a particular entity, other embodiments are possible in which these tasks are performed by a different entity.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, the processes described herein can be embodied within a form that does not provide all of the features and benefits set forth herein, as some features can be used or practiced separately from others. The scope of protection is defined by the appended claims rather than by the foregoing description. All changes which come within the meaning and range of equivalency of the claims are to be embraced within their scope.

What is claimed is:

1. A biometric and performance monitoring system, comprising:
   a computer having a mouse and a keyboard electronically coupled thereto;
   a pulse oximeter sensor and a galvanic-skin resistance sensor disposed in the mouse, the pulse oximeter sensor and the galvanic-skin resistance sensor being electrically coupled to the computer;
   at least one sensor disposed in the keyboard and being electrically coupled to the computer, the pulse oximeter sensor, galvanic-skin sensor, and the at least one sensor of the keyboard being configured to measure biometric parameters of a user;
   a computer-readable storage medium associated with the computer, the computer readable storage medium adapted for storing the biometric parameters and performance parameters measured by the mouse and the keyboard;
   wherein the computer is configured to analyze the biometric parameters within the context of the performance parameters associated with the mouse and the keyboard for indications of impairment of a user;
   wherein, responsive to a determination by the computer that there are indications of impairment of a user the computer is configured to initiate a corrective action comprising sending at least one of an alert to the user, an electronic communication to a medical service provider, and an electronic communication to a supervising entity.

2. The biometric and performance monitoring system of claim 1, wherein the mouse includes a skin-temperature sensor.

3. The biometric and performance monitoring system of claim 2, wherein the skin-temperature sensor is disposed on a side surface of the mouse.

4. The biometric and performance monitoring system of claim 1, wherein the at least one sensor of the keyboard includes an electrocardiogram.

5. The biometric and performance monitoring system of claim 1, wherein the galvanic-skin resistance sensor is disposed on a top surface of the mouse.

6. The biometric and performance monitoring system of claim 1, wherein the computer-readable storage medium is remote from the computer.

7. The biometric and performance monitoring system of claim 1, wherein the computer communicates with the medical service provider and the supervising entity via at least one of a wired connection and a wireless connection.

8. The biometric and performance monitoring system of claim 1, wherein analysis of the biometric parameters and the performance parameters occurs in real time or near real time.

9. The biometric and performance monitoring system of claim 1, wherein the computer analyzes the biometric parameters within the context of the performance parameters.

10. A non-transitory storage medium having stored thereon logic that, upon execution, causes operations including:

obtaining, via sensors associated with a mouse and a keyboard, biometric parameters from a user, the mouse comprising a pulse oximeter sensor and a galvanic-skin resistance sensor;

storing the biometric parameters in a computer-readable storage medium associated with a computer that is electronically coupled to the sensors associated with the mouse and keyboard;

obtaining, via the computer, performance parameters associated with the mouse and keyboard;

determining a base-line data set from the biometric parameters and the performance parameters;

analyzing the biometric parameters and the performance parameters to determine variations from the base-line data set; and responsive to a determined variation from the base-line data set, initiating a corrective action comprising sending at least one of an alert of possible user impairment to a user, a medical service provider, and a supervising entity;

wherein the analyzing comprises interpreting the biometric parameters within the context of the performance parameters for indications of impairment of a user.

11. The non-transitory storage medium of claim 10, wherein the operations further include measuring, via the at least one sensor of the keyboard, an electrocardiogram.

12. The non-transitory storage medium of claim 10, wherein the performance parameters include at least one of mouse strain exposure, hours of computer usage, number of breaks skipped, a degree that breaks were postponed, mouse clicks, distance a mouse has moved, number of mouse double clicks, number of mouse left clicks, number of mouse right clicks, number of scroll clicks, minutes from midnight the first activity occurred, and minutes from midnight the last activity occurred.

13. The non-transitory storage medium of claim 10, wherein the interpreting is responsive to a determined variation from the base-line data.

14. The non-transitory storage medium of claim 10, wherein analysis of the biometric parameters and the performance parameters occurs in real time or near real time.

15. A biometric and performance monitoring system, comprising:

a computer having a mouse and a keyboard electronically coupled thereto;

a pulse oximeter sensor and a galvanic-skin resistance sensor disposed in the mouse, each being electrically coupled to the computer;

at least one sensor embedded in the keyboard and being electrically coupled to the computer; and a computer-readable storage medium associated with the computer, the computer-readable storage medium adapted for storing biometric parameters and performance parameters measured with the sensors of the mouse and the keyboard, and configured to interpret the biometric parameters within the context of the performance parameters for indications of impairment of a user.

16. The system of claim 15, wherein the mouse further comprises an accelerometer that is electrically coupled to the computer.

17. The system of claim 15, wherein the mouse further comprises a skin temperature sensor that is electrically coupled to the computer.

* * * * *